United States Patent
Ono et al.

(10) Patent No.: US 7,365,768 B1
(45) Date of Patent: Apr. 29, 2008

(54) ENDOSCOPE APPARATUS AND FUNCTION ADJUSTING CIRCUIT FOR ENDOSCOPE

(75) Inventors: Mitsunobu Ono, Tokyo (JP); Masanao Murata, Tokorozawa (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 09/483,883

(22) Filed: Jan. 18, 2000

(30) Foreign Application Priority Data

Jan. 21, 1999 (JP) .................................. 11-013328

(51) Int. Cl.
*H04N 7/18* (2006.01)

(52) U.S. Cl. .............................. 348/76; 348/65; 348/72; 348/77; 600/109; 600/112; 600/114; 600/101; 600/130

(58) Field of Classification Search .................. 348/76, 348/445, 220.1, 335, 458, 72, 69, 45, 77, 348/74, 68, 65, 70, 376, 521, 518; 600/152, 600/117, 101, 139, 114, 109, 112, 130; 388/838

See application file for complete search history.

(56) References Cited

U.S. PATENT DOCUMENTS

| | | | | |
|---|---|---|---|---|
| 4,559,928 A | * | 12/1985 | Takayama | 600/152 |
| 4,646,724 A | * | 3/1987 | Sato et al. | 348/68 |
| 4,831,444 A | * | 5/1989 | Kato | 348/518 |
| 4,845,555 A | * | 7/1989 | Yabe et al. | 348/72 |
| 4,941,456 A | * | 7/1990 | Wood et al. | 348/69 |
| 5,040,068 A | * | 8/1991 | Parulski et al. | 348/376 |
| 5,368,015 A | * | 11/1994 | Wilk | 600/104 |
| 5,614,943 A | * | 3/1997 | Nakamura et al. | 348/72 |
| 5,627,583 A | * | 5/1997 | Nakamura et al. | 348/72 |
| 6,099,465 A | * | 8/2000 | Inoue | 600/134 |
| 6,100,920 A | * | 8/2000 | Miller et al. | 348/68 |
| 6,215,517 B1 | * | 4/2001 | Takahashi et al. | 348/72 |

FOREIGN PATENT DOCUMENTS

JP         63-283277        11/1988

* cited by examiner

*Primary Examiner*—Shawn S. An
(74) *Attorney, Agent, or Firm*—Ostrolenk, Faber, Gerb & Soffen, LLP

(57) ABSTRACT

An endoscope includes an insert section, a CCD is mounted at the end of the insert section, and a CCU for producing a video signal is arranged in a control unit connected to a proximal end of the insert unit. The CCU includes a general-purpose DSP board having the function of producing a standard video signal, and a function adjustment/expansion circuit board for correcting a signal delay due to the length of a signal line connected to the CCD. The DSP boards and the function adjustment/expansion circuit boards, respectively remaining the same in circuit arrangement, are used for a plurality of types of endoscopes having insert sections having different insertion lengths.

14 Claims, 12 Drawing Sheets

FIG.4
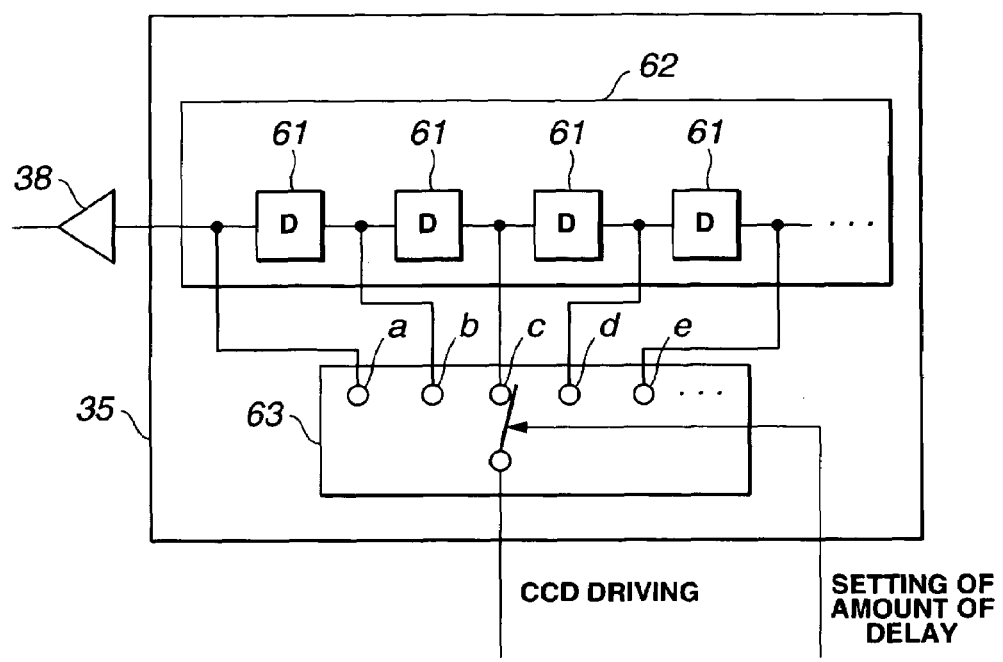
FIG.5A φH (NO DELAY)
FIG.5B φH (LONG SIGNAL LINE LENGTH)
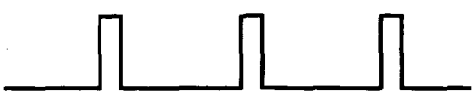
FIG.5C φH (MEDIUM SIGNAL LINE LENGTH)
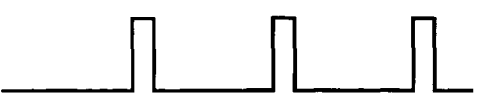
FIG.5D φH (SHORT SIGNAL LINE LENGTH)

FIG.6
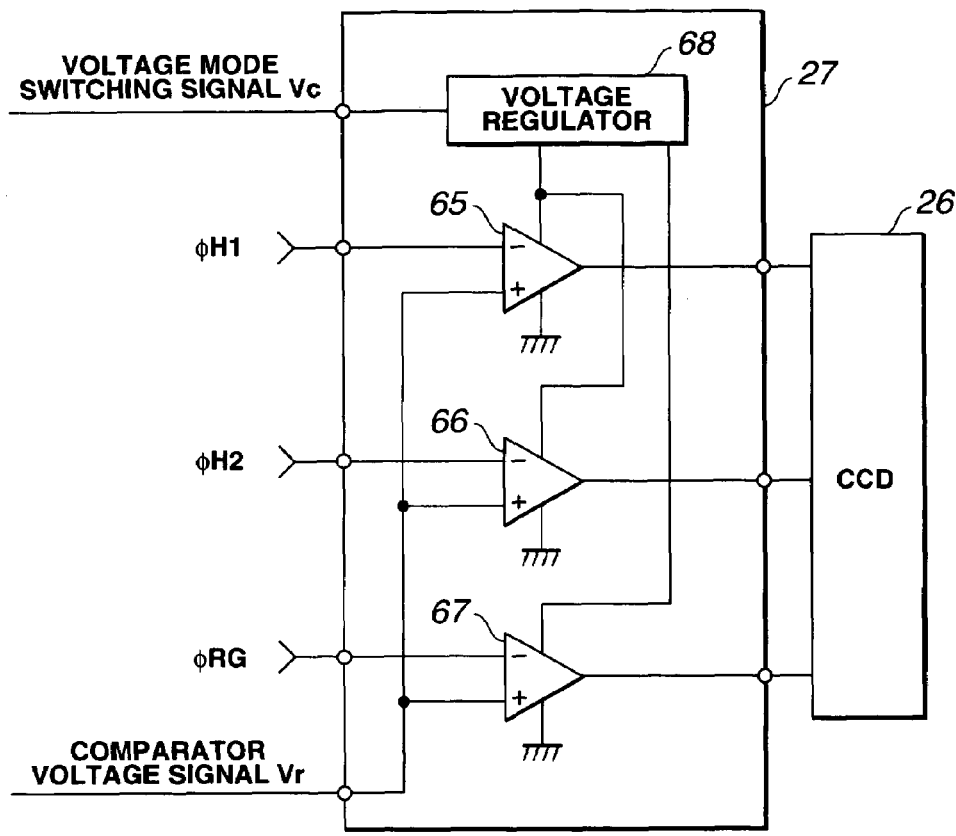
FIG.7A INPUT SIGNAL φRG
FIG.7B OUTPUT SIGNAL φRG
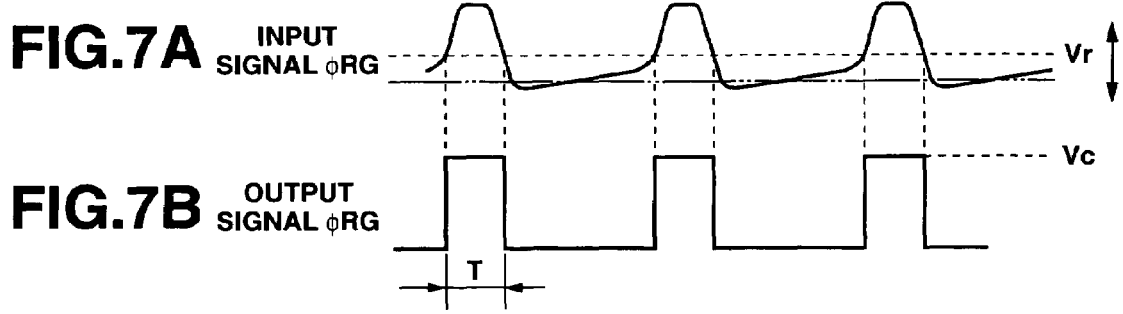

ENDOSCOPE APPARATUS AND FUNCTION ADJUSTING CIRCUIT FOR ENDOSCOPE

BACKGROUND OF THE INVENTION

1. Field of the Invention

The present invention relates to an endoscope apparatus having a general-purpose video signal processing circuit which is provided with an adjustment function or expanded function, such as signal processing, adapted for use in a solid-state image pickup device built in an endoscope and to an endoscopic function adjusting circuit.

2. Description of the Related Art

As disclosed in Japanese Unexamined Patent Publication No. 63-283277, an endoscope apparatus having an image pickup device tends to become complex in the structure of the circuit therein because of the necessity of correcting a signal delay due to a cable running through the insert section thereof and correcting the waveform of a CCD drive pulse.

For this reason, in the conventional art, all signal processing circuits for driving an image pickup device and processing an output signal of the image pickup device are built in an endoscope side. The endoscope having the built-in image pickup device needs signal processing circuits including a CDS circuit, an AGC circuit, an A/D converter, an encoder, etc.

In the conventional art, each of the signal processing circuits built in the endoscope needs to be developed as a circuit dedicated to the endoscope. Since each circuit needs to be developed and prepared each time the need arises, the circuit lacks versatility. If many models of endoscopes are manufactured in a production system, of which a large-inventory and small-production quantity method is currently required, circuits need to be newly developed and prepared in accordance with the types of endoscopes, and development costs involved increase.

SUMMARY OF THE INVENTION

It is an object of the present invention to provide an endoscope apparatus having a signal processing circuit that is low-cost and compatible with a number of models of endoscopes, and to a function adjusting circuit for the endoscopes.

It is another object of the present invention to provide an endoscope apparatus which is realized at a low cost by adding an endoscopic function adjusting circuit specific to a common general-purpose signal processing circuit to be compatible with many models of endoscopes having insert sections having insertion lengths, and an endoscopic function adjusting circuit for the endoscope.

An endoscope apparatus of the present invention includes a solid-state image pickup device mounted at the end of an insert section of an endoscope and a signal processing circuit, arranged in the endoscope, for driving the solid-state image pickup device and for producing a standard video signal in response to an output signal from the solid-state image pickup device, wherein the signal processing circuit comprises a general-purpose video signal processing circuit having a drive signal generation function for driving the solid-state image pickup device and a signal processing function for outputting the standard video signal by processing the output signal from the solid-state image pickup device, and an endoscopic function adjusting circuit comprising a function modifying circuit, connected to the general-purpose video processing circuit, for modifying at least one of the drive signal processing function and the signal processing function executed by the general-purpose video signal processing circuit to perform signal processing compatible with the solid-state image pickup device mounted at the end of the insert section.

An endoscopic function adjusting circuit of the present invention, connected to a general-purpose video processing circuit, for driving a solid-state image pickup device built in an endoscope, and for outputting a standard video signal by processing an output signal of the solid-state image pickup device, includes a function modifying circuit for modifying at least one of the drive signal processing function and the signal processing function executed by the general-purpose video processing signal in accordance with the endoscope having the solid-state image pickup device therein.

Other features and advantages of the present invention will become apparent from the following description.

BRIEF DESCRIPTION OF THE DRAWINGS

FIG. 1 through FIG. 7 show a first embodiment of the present invention, wherein FIG. 1 is a block diagram showing the general construction of an endoscope system of the present invention, FIG. 2 is a block diagram showing the construction of an endoscope apparatus, FIG. 3 is a block showing the internal construction of a DSP, FIG. 4 is a circuit diagram showing the construction of a DL delay circuit, FIG. 5 is a diagram explaining the operation of the circuit shown in FIG. 4, FIG. 6 is a circuit diagram showing the construction of an HIC circuit, and FIG. 7 is a diagram explaining the operation of the circuit shown in FIG. 6, and FIG. 8 and FIG. 9 show a second embodiment of the present invention, wherein FIG. 10 and FIG. 11 show a third embodiment of the present invention, wherein FIG. 10 is a block diagram showing the construction of an endoscope apparatus, and FIG. 11 is a block diagram showing the construction of an electrical system of an endoscope apparatus, and FIG. 12 and FIG. 13 show a fourth embodiment of the present invention, wherein FIG. 12 is a block diagram showing the general construction of an endoscope system, and FIG. 13 is a block diagram showing the construction of an electrical system of an endoscope apparatus.

DESCRIPTION OF THE PREFERRED EMBODIMENTS

Figure 1:
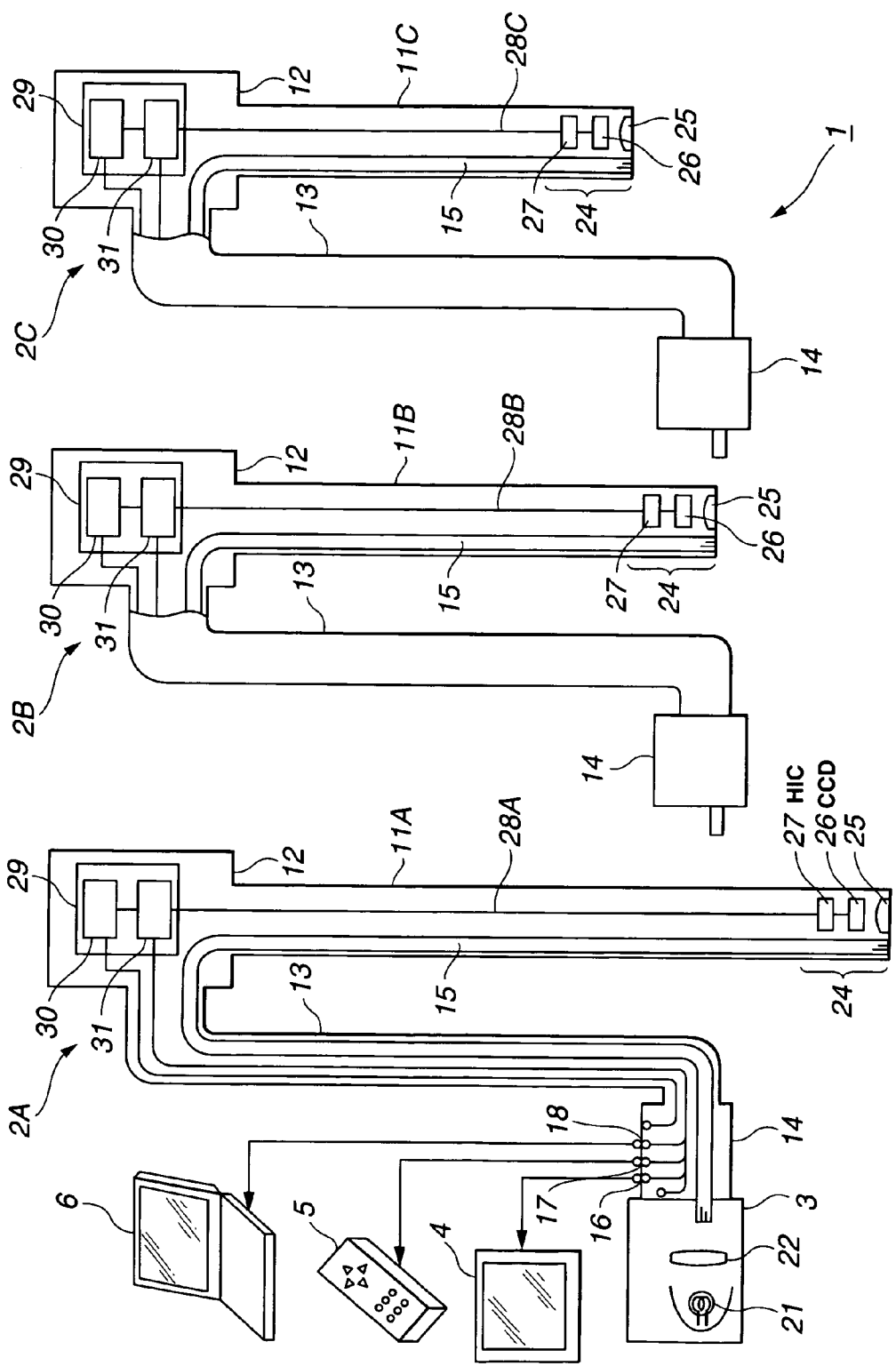

The embodiments of the present invention are now discussed, referring to the drawings.

First Embodiment

Figure 2:
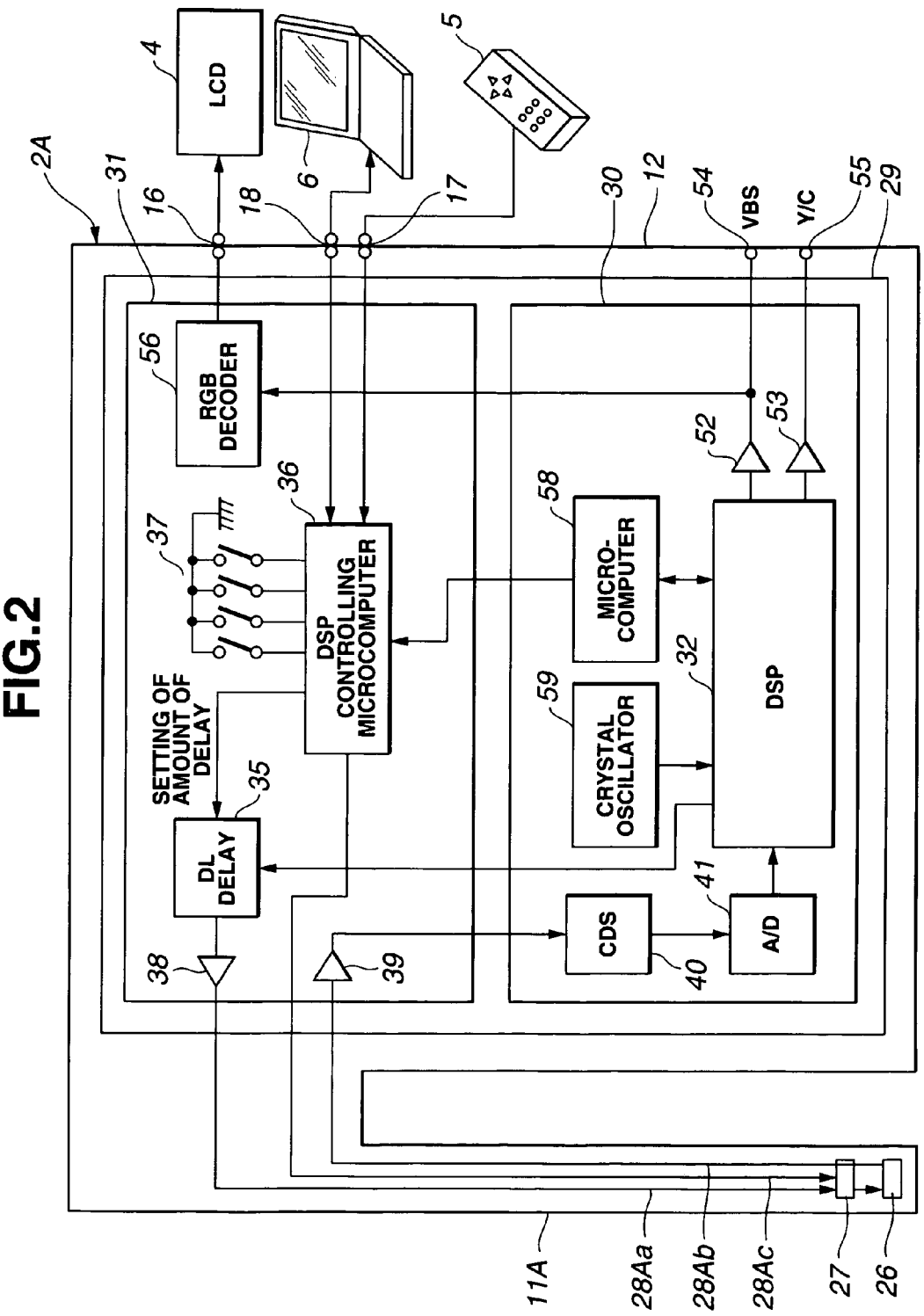
Figure 3:
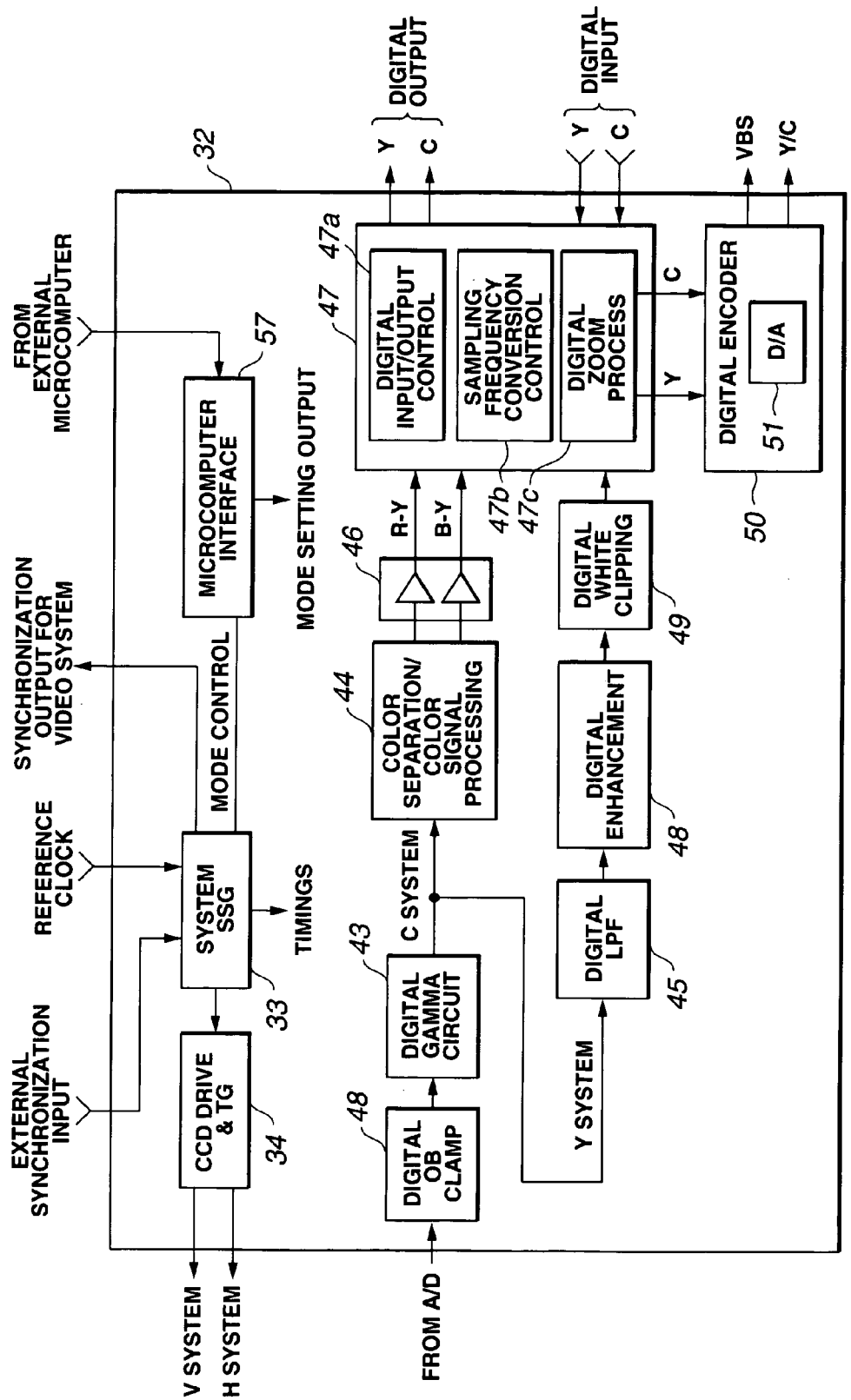

FIG. 1 through FIG. 7 show a first embodiment of the present invention, wherein FIG. 1 is a block diagram showing the general construction of an endoscope system of the first embodiment of the present invention, FIG. 2 is a block diagram showing the construction of an endoscope apparatus, FIG. 3 is a block showing the internal construction of a DSP, FIG. 4 is a circuit diagram showing the construction of a DL delay circuit, FIG. 5 is a diagram explaining the operation of the circuit shown in FIG. 4, FIG. 6 is a circuit diagram showing the construction of a hybrid IC circuit, and FIG. 7 is a diagram explaining the operation of the circuit shown in FIG. 6.

Referring to FIG. 1, an endoscope system 1, incorporating the first embodiment of the present invention, includes a plurality of endoscopes 2A, 2B, and 2C, each containing its own image pickup means, a light source device 3 for supplying illumination light to an endoscope 2I (I=A, B, or C) connected thereto, a liquid-crystal display monitor 4 for displaying an endoscopic image picked up, an operational remote control unit (simply referred to as remote control) 5, detachably connected to an external remote control terminal of the endoscope 2I, for performing a zooming operation, and a personal computer (simply referred to as a computer) 6, detachably connected to a serial terminal of the endoscope 2I, for exchanging data.

The endoscope 2I includes an elongated insert section 11I being different in length, a control section 12 arranged at the proximal end of the insert section 11I, and a universal cable 13 that is extended from one side of the control section 12, and the incident end of a light guide 15 extending from a connector 14 on the other end of the universal cable 13 is detachably connected to the light source device 3.

A video terminal 16, an external remote terminal 17, and a serial terminal 18 arranged on the connector 14 are respectively connected to the liquid-crystal display monitor 4, the remote control 5, and the computer 6 via respective interconnect cables.

A lamp 21, such as a halogen lamp, is arranged in the light source device 3, and white light emitted from the lamp 21 is condensed by a condenser lens 22 and is then directed to the end face of the light guide 15.

Illumination light, transmitted through the light guide 15 running through the endoscope 2I, is forwardly projected through the end face of the light guide fixed to an illumination window of an end portion 24 of the insert section 11I to illuminate an object, such as a lesion of a subject.

The end portion 24 has an observation window (an image pickup window) next to the illumination window, and an objective lens 25 is mounted on the observation window, and a charge-coupled device (simply referred to as CCD) 26 is arranged at a focus position of the objective lens 25, and photoelectrically converts an optical image. The endoscope 2I in this embodiment is thus an electronic endoscope having a CCD 26 at the end portion 24 of the insert section 11I.

A color separation filter, such as an unshown mosaic filter, is arranged on the imaging surface (a photosensitive surface) of the CCD 26, performing color separation on a per pixel basis.

In this embodiment, a hybrid integrated circuit (simply referred to as HIC) 27 having a wave shaping function is arranged in the end portion 24, namely, in the vicinity of the CCD 26, and wave-shapes a CCD drive signal, transmitted through a signal line 28I, for driving the CCD 26 before applying it to the CCD 26.

The CCD 26 is connected, via the signal line 28I, to a camera control unit (simply referred to as CCU) 29, which is a video signal processing circuit arranged in the control section 12.

In this embodiment, the CCU 29 includes a DSP board 30 having a digital signal processor (simply referred to as DSP) thereon as a general-purpose board with a function for generating a standard video signal, and a function adjustment/expansion circuit board 31I, connected to the DSP board 30, having function adjusting (function modification) means or function expansion means compatible with functions specific to the endoscope.

Since the DSP board 30 has the function of generating the standard video signal, a monitor displays an image picked up by the CCD 26 if the DSP board 30 (CCD drive circuit) is connected to the CCD 26 directly (or via a short cable) with the video signal output terminal thereof connected to the monitor.

Specifically, the DSP board 30 has the CCD drive function to generate a CCD drive signal to the CCD 26 and the video signal processing function to generate the standard video signal by processing the CCD drive signal output by the CCD 26 in response to the CCD drive signal. The function adjustment/expansion circuit board 31 has the function modification means or the function expansion means corresponding to functions (for example, a function of canceling the effect of a signal delay) that are required of the endoscope 2I which has insert section 11I different in length from type to type (therefore, having a signal delay amount dependent on the length of the signal line 28I between the CCD 26 and the CCU 29). In this embodiment, the DSP board 30, with the function adjustment/expansion circuit board 31 connected thereto, works with the endoscope 2I having a different insertion length (cable length) (in other words, performing signal processing compatible with the CCD 26 that is arranged on the end portion of the insert section in the endoscope 2I having a different insertion length).

In this embodiment, the function adjustment/expansion circuit board 31 has a different set value for the endoscope 2A (the CCD 26 arranged at the end portion of the insert section 11I when the insertion length is different) depending on the insertion length (cable length). Even when the insertion length is different, the common function adjustment/expansion circuit board 31 is set to work, thereby reducing costs of the apparatus.

In the present embodiment, the CCU 29 is supplied with power required for the operation thereof by an unshown power supply circuit in the light source device 3.

FIG. 2 shows the construction of an electrical system of the endoscope apparatus having the endoscope 2A, for example. The DSP board 30 includes a DSP 32 having (a CCD drive function and) a signal processing function. In the DSP 32, as shown in FIG. 3, a CCD drive & TG circuit 34 generates a CCD drive signal and a timing signal (simply referred to as TG) in synchronization with a timing signal of a system signal generator circuit (simply referred to as an SSG circuit) 33 in the DSP 32. The CCD drive signal and the timing signal are fed to a delay line delay circuit (simply referred to as DL delay circuit) 35, and are adjusted by the DL delay circuit 35 in timing corresponding to the cable length (signal line length) in accordance with a delay amount setting signal coming from a DSP controlling microcomputer (simply referred to as DSP controlling computer) 36.

The DSP controlling computer 36 is connected to a DIP switch 37, for instance, and outputs, to the DL delay circuit 35, a corresponding delay amount setting signal of a plurality of bits in response to a combination of ON/OFF settings of the DIP switch 37.

The output signal of the DL delay circuit 35 is amplified by a drive amplifier 38, then applied to a HIC 27 through a drive signal line 28Aa forming the signal line 28A, waveshaped by the HIC 27, and then fed to the CCD 26 arranged in the vicinity of the HIC 27.

In response to the application of the CCD drive signal, the CCD 26 gives a photoelectrically converted CCD output signal, and the CCD output signal is fed to a preamplifier 39 in the function adjustment/expansion circuit board 31 for amplification through an output signal line 28Ab forming the signal line 28A, and is fed to a correlated double sampling circuit (simply referred to as CDS circuit) 40 in the DSP board 30, and a signal component is extracted from the CCD output signal.

As will be discussed later, the CDS circuit 40 extracts the signal component from a signal portion in response to a sampling pulse at a correct timing in the same manner as in the case when no signal delay takes place, because of the signal delay in the CCD drive signal provided by the DL delay circuit 35.

The output signal of the CDS circuit 40 is converted through an A/D converter circuit 41 into a digital signal, which is then fed to a digital optical black clamp circuit (simply referred to as digital OB clamp circuit) 42 in the DSP 32. A process is performed to set, to a black level, an output signal level in an OB section in each of all pixels in the CCD 26, where light is blocked, and then the signal is fed to a digital gamma circuit 43.

After being subjected to gamma correction through the digital gamma circuit 43, the output of the CDS circuit 40 is fed to a color separation/color signal processing circuit 44 for performing color separation and color signal processing and to a digital low-pass filter circuit (simply referred to as digital LPF circuit) 45.

The color separation/color signal processing circuit 44 subjects the above signal to color separation and color signal processing, resulting in color-difference signals R-Y and B-Y (U and V) as color signals C, which are then input to a white balance variable amplifier 46. After being white balance adjusted, the color signals C are then input, to a digital control and processing unit 47 including a digital input and output controller 47a for controlling digital input and output, a sampling frequency conversion controller 47b for controlling sampling frequency conversion, and a digital ZOOM processor 47c for processing digital zooming.

In this embodiment, the white balance variable amplifier 46 performs white balance adjustment when the lamp 21 in the light source device 3 is a light source lamp.

After being extracted from the signal input to the digital LPF circuit 45, a digital luminance signal Y component is fed to a digital enhancement circuit 48, where horizontal and vertical enhancements are performed thereon. The resulting luminance signal Y component is input to a digital white clipping circuit 49, where the luminance signal is clipped at a white level. The clipped signal is then fed to the digital control and processing unit 47.

The digital luminance signal Y and the color signals C output by the digital control and processing unit 47 are fed to a digital encoder circuit 50. The digital encoder circuit 50 converts these signals into a digital composite video signal (composite signal) VBS in which the luminance signal Y, the color signals C and the synchronization signal are superimposed, and Y/C separate signals (Y/C component signals) containing the luminance signal Y and the color signals C. The digital composite video signal VBS and the digital Y/C separate signals are converted by a D/A converter circuit 51 into an analog composite video signal VBS and analog Y/C separate signals, which are then respectively output from a composite video signal output terminal 54 and a Y/C separate video signal output terminal (S terminal) 55 via buffer amplifiers 52 and 53 as shown in FIG. 2.

The composite video signal VBS output from the buffer amplifier 52 is input to an RGB decoder 56 in the function adjustment/expansion circuit board 31 and is converted into an RGB signal for driving the liquid-crystal display monitor 4. An object is thus displayed in color on the liquid-crystal display monitor 4.

The digital control and processing unit 47 outputs the digital luminance signal Y and the digital color signals (color-difference signals R-Y and B-Y, or U and V) at a ratio of Y:U:V=4:2:2 (or Y:U:V=4:2:0) while controlling and processing the digital luminance signal Y and the digital color signals C input thereto at a ratio of Y:U:V=4:2:2 (or Y:U:V=4:2:0).

The DSP board 30 includes the DSP 32 and a microcomputer 58 for bilaterally exchanging information through an internal microcomputer interface 57. The microcomputer 58 is connected to the DSP controlling computer 36 in the function circuit board 31 through a serial interface, for instance, and changes or sets an operation mode of the DSP 32 through the DSP controlling computer 36.

The system SSG circuit 33 in the DSP 32 is supplied with a reference clock, from a crystal oscillator circuit 59 in the DSP board 30, used to read data from pixels of the CCD 26. In synchronization with the reference clock, the system SSG circuit 33 generates and outputs a variety of timing signals including a synchronization signal for the video system. Receiving an external synchronization signal at the external synchronization input terminal, the system SSG circuit 33 generates a variety of timing signals in synchronization with the external synchronization signal.

In this embodiment, the DSP controlling computer 36 is connected to the HIC 27 through a signal line 28Ac so that the DSP controlling computer 36 changes the wave shaping operation mode by the HIC 27.

FIG. 4 shows the construction of the DL delay circuit 35. For instance, the DL delay circuit 35 includes a delay unit 62 having a number of connected delay lines or delay elements (labeled D in FIG. 4) 61 for a constant time delay, and a multiplexer (or a selection switch) 63 for selecting and setting the amount of delay by selecting a junction j (j=a, b, c, d, e, . . . ) connected to the delay lines 61. The selection of the junction j by the multiplexer 63 is determined in response to the delay amount setting signal from the DSP controlling computer 36.

The DL delay circuit 35 corrects the time delay in the CCD drive signal and the CCD output signal due to the insertion length or the cable length.

For instance, in the endoscope 2A having the longest cable length, the endoscope 2B having the medium cable length, and the endoscope 2C having the shortest cable length, the delay time is set for a horizontal transfer signal φH of the CCD drive signal as shown in FIG. 5(B), FIG. 5(C), and FIG. 5(D) so that the phase thereof is advanced by the delay time due to the cable length from a (next) horizontal transfer signal φH when no delay is introduced as shown in FIG. 5(A) (meaning that the CCD 26 is installed in the CCU 29) and the input timings of the CCD output signal into the CDS circuit 40 are aligned without dependence on the cable length.

The CDS circuit 40 extracts the signal component at the CDS sampling pulse (at the timing of the horizontal transfer signal φH without considering the cable length as shown in FIG. 5(A)), thereby extracting the signal of the CCD output signal at the timing when the signal is input (even when the cable length is changed).

For simplification, as shown in FIG. 5, the signal delay amount is shorter than a duration corresponding to a single pixel even in the endoscope 2A having the longest cable length. When the signal delay amount is longer than the duration corresponding to a single pixel, the timing is synchronized with the horizontal transfer signal φH with no delay introduced, after a duration corresponding to two pixels or three pixels.

Referring to FIG. 5, the horizontal transfer signal φH is shown. Besides this, a reset gate pulse φR and a vertical transfer pulse φV are similarly time-delayed through the DL delay circuit 35.

In this way, the CDS circuit 40 and the like are aligned with the timing of the CCD output signal with no delay, thereby extracting the signal component of the CCD output signal.

A buffer or the like may be used for the delay line (delay element) 61, and the delay amount is changed by the number of stages of the buffer.

Since the wave of the CCD drive signal applied to the CCD 26 is subject to change depending on the cable length, the HIC 27 for wave shaping is arranged in the vicinity of the CCD 26 in this embodiment to shape the wave of the CCD drive signal.

FIG. 6 shows the construction of the HIC 27 as a wave shaping circuit.

The HIC 27 includes comparators 65, 66, and 67 for performing wave shaping in response to input two-phase horizontal transfer signals φH1 and φH2, and reset gate signal φRG of the CCD drive signal, and a voltage regulator 68 for determining the output levels of the comparators 65, 66, and 67.

The horizontal transfer signals φH1 and φH2 and the reset gate signal §RG are fed to respective inverting input terminals of the comparators 65, 66, and 67, and a common comparator voltage signal Vr is fed to non-inverting input terminals of the comparators 65, 66, and 67. The comparator voltage signal Vr is applied from the DSP controlling computer 36 through the signal line 28Ac.

The voltage regulator 68 is supplied with a voltage mode switching signal Vc from the DSP controlling computer 36 through the signal line 28Ac. The voltage mode switching signal Vc at an "L" level or an "H" level in accordance with the type of the CCD 26 is applied to the voltage regulator 68. The voltage regulator 68 feeds a power source voltage at a corresponding voltage level (5 V or 8 V, for instance) to the power supply terminals of the comparators 65, 66, and 67. The comparators 65, 66, and 67 supply the CCD 26 with the CCD drive signals at the required voltage level.

FIG. 7 shows the operation of the HIC 27 shown in FIG. 6. Referring to FIG. 7(A), the reset gate signal φRG is input to the comparator 65, as an input signal (for the comparator) having the wave thereof deformed through the cable, and is compared with the comparator voltage signal Vr. As a result, a wave-shaped output signal φRG shown in FIG. 7(B) is output.

FIG. 7 shows the reset gate signal φRG, and the horizontal transfer signals φH1 and φH2 are also similarly shaped.

By variably setting the level of the comparator voltage signal Vr in this embodiment, the CCD 26 is supplied with the reset gate signal φRG having a proper pulse width T unaffected by sagging thereof. For instance, at a level represented by a two-dot chain line as shown in FIG. 7(A), supplying the CCD 26 with an appropriate reset gate signal φRG is difficult under the effect of the sagging. In this embodiment, even if the wave of the CCD drive signal is deformed depending on the cable length, the comparator voltage signal Vr is set according to the wave deformation due to the cable length. The CCD 26 is thus constantly supplied with the CCD drive signal having an appropriate pulse width T.

When the CDS circuit 40 extracts the signal component from the CCD output signal, the extraction timing is prevented from being slipped.

In accordance with the present embodiment, the CCD 26 is arranged on the end portion 24 of the insert section 11I of the endoscope 2I having a different insertion length, and when the cable length to the CCU 29 in the endoscope 2I is different, the signal processing appropriate to each CCD 26 is carried out.

In this case, the CCU 29 includes the common DSP board 30 and the function adjustment/expansion circuit board 31 having a different delay set in the drive signal in accordance with the insertion length (cable length) so that the CCU 29 is compatible with each CCD even with the insertion length different. With a low cost involved, the CCU 29 thus works with the endoscope 2I having a different insertion length.

Second Embodiment

Figure 8:
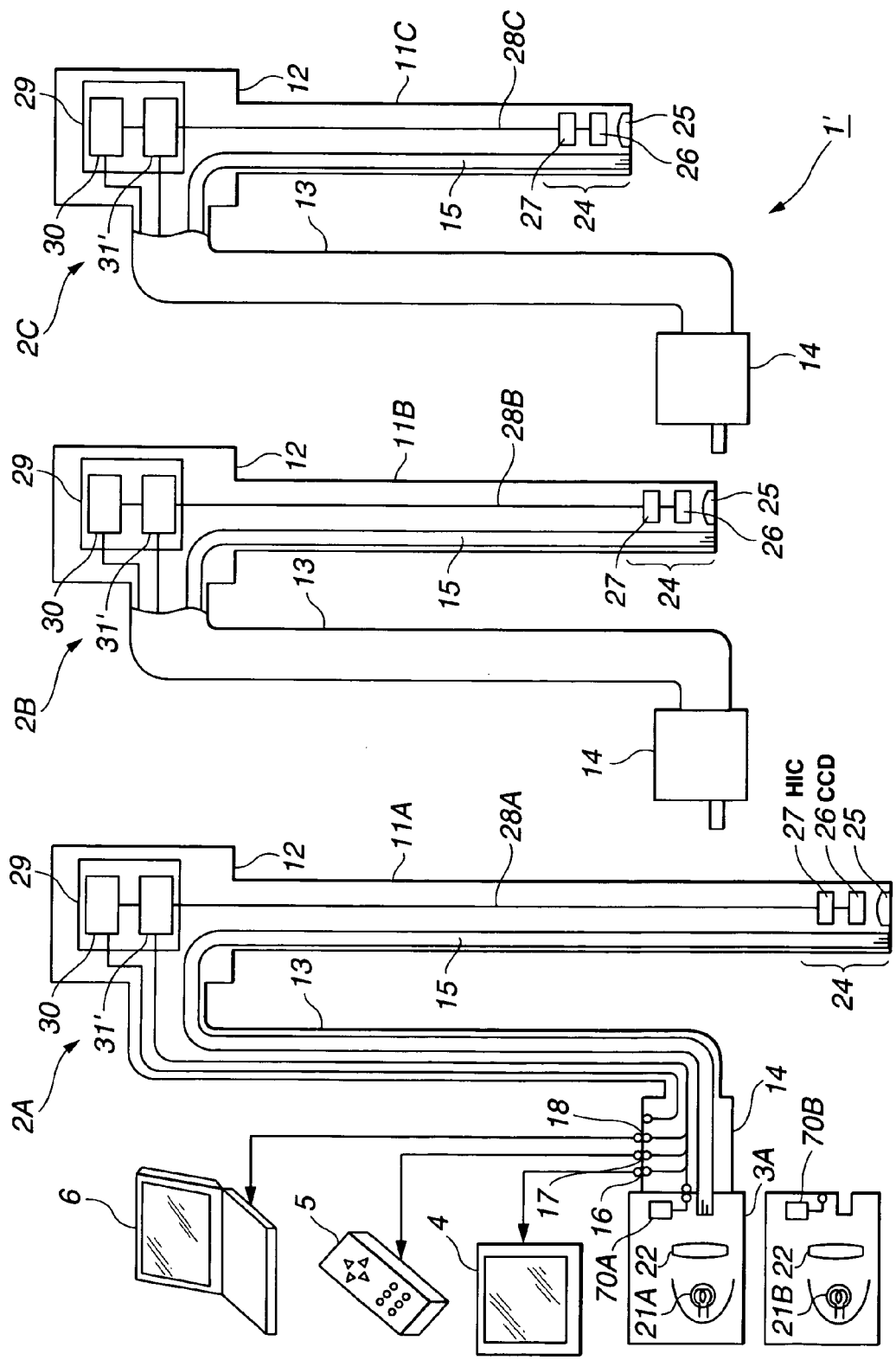
FIG. 8 is a block diagram showing the general construction of an endoscope system.
Figure 9:
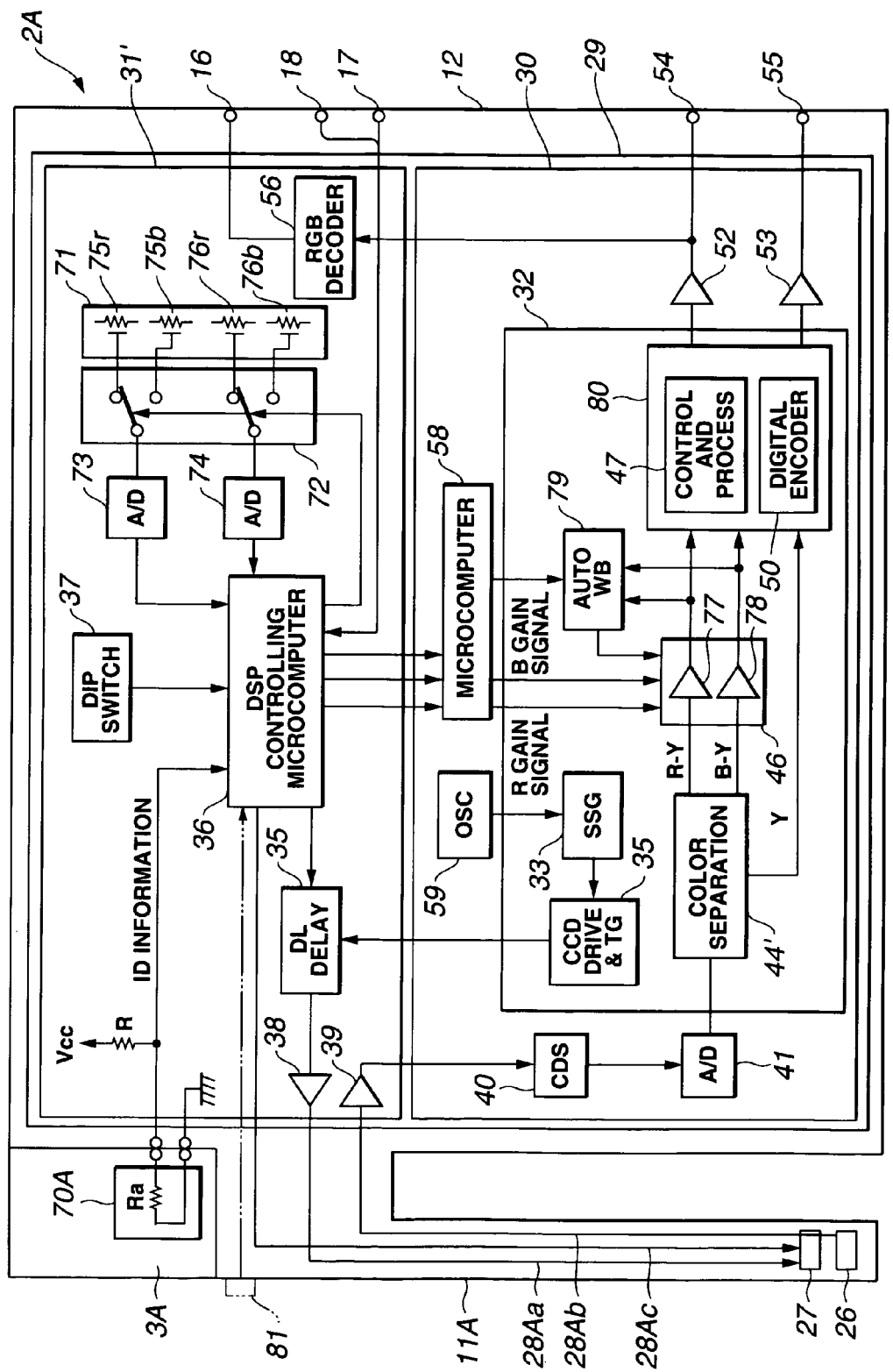
FIG. 9 is a block diagram showing the construction of an endoscope apparatus.

A second embodiment of the present invention is now discussed, referring to FIG. 8 and FIG. 9. FIG. 8 shows an endoscope system 1' of the second embodiment. The endoscope system 1 employs one of a light source device 3A of a metal halide lamp 21A and a light source device 3B of a xenon lamp 21B, instead of the light source 3 in the endoscope system 1 shown in FIG. 1.

Since the metal halide lamp 21A and the xenon lamp 21B are different from each other in color temperature (the wavelength distribution of emitted light), white balance adjustment is needed at different settings. For this reason, the CCU 29 in the endoscope 2I is provided with means for setting white balance corresponding to the light source device 3A or 3B depending on whether the light source 3A or 3B is in use. In this embodiment, the CCU 29 includes the DSP board 30 identical to the one in the first embodiment, and a function adjustment/expansion circuit board 31' including white balance setting means respectively corresponding to the light sources 3A and 3B, instead of the function adjustment/expansion circuit board 31 in the first embodiment. The light sources 3A and 3B respectively include identification signal generator circuits 70A and 70B for generating unique identification information (ID information).

When mounted, the signal from the identification information signal generator circuit 70A or 70B respectively arranged in the light source device 3A or 3B is input to the DSP controlling computer 36 in the function adjustment/expansion circuit board 31' as shown in FIG. 9.

FIG. 9 shows the construction of an electrical system of the endoscope 2A to which the light source device 3A is connected. When the light source device 3A is connected to the endoscope 2A, the identification signal generator circuit 70A, including a resistor Ra (a resistor Rb in the light source device 3B), for instance, provides, to the DSP controlling computer 36, the identification information indicating the type of the light source lamp (the metal halide lamp 21A here) at a voltage level determined by dividing the power source voltage Vcc by a reference resistor R and the resistor Ra.

The function adjustment/expansion circuit board 31' includes a gain setting circuit 71 for setting gains for a plurality of color signals in accordance with the type of the light source lamp. The output of the gain setting circuit 71 is fed to A/D converters 73 and 74 via a selector 72 to be converted into digital signals, which are then fed to the DSP controlling computer 36 (the A/D converters 73 and 74 are dispensed with if the DSP controlling computer 36 has the A/D conversion function).

Specifically, the gain setting circuit 71 includes gain setting potentiometers 75r and 76r for setting gains for the color signals of R and B with the G color signal set as a reference, and gain setting potentiometers 75b and 76b for setting gains for the color signals of R and B for setting the white balance in the xenon lamp 21B.

The signal from the gain setting potentiometers 75r and 75b for the color signal of R and the signal from the gain setting potentiometers 76r and 76b for the color signal of B are fed to the A/D converters 73 and 74 via the selector 72 to be converted into the digital signals, which are then fed to the DSP controlling computer 36.

The DSP controlling computer 36 generates a selection signal from the ID information, and selects the R gain and B gain of the light source corresponding to the ID information through the selector 72. When the light source device 3A is connected as shown in FIG. 8, the DSP controlling computer 36 receives the R gain and B gain (namely, voltage values across the resistors determining the R gain and B gain) determined by the gain setting potentiometers 75r and 76r for setting the white balance in the wavelength distribution of the illumination light of the metal halide lamp 21A therein as a light source.

The DSP controlling computer 36 feeds, via the microcomputer 58 in the DSP board 31, an R gain controlling signal and B gain controlling signal to gain control terminals of dual variable amplifiers 77 and 78 in the white balance variable amplifier 46 in the DSP 32. The DSP controlling computer 36 thereby sets a white balance state to match the metal halide lamp 21A.

The DSP controlling computer 36 feeds, via the microcomputer 58, an auto gain stop signal to an auto white balance circuit 79 in the DSP 32 to stop the operation of the auto white balance circuit 79. Although the discussion of the auto white balance circuit 79 is omitted in conjunction with the first embodiment, the DSP 32 for performing general-purpose video signal processing is typically provided with the auto white balance circuit 79. The auto white balance circuit 79 automatically sets the white balance by adjusting the R and B gains so that the averages of the color signals in the signal picked up from light reflected from an object under the natural light are balanced.

To this end, in this embodiment, the white balance is precisely set in response to the wavelength distribution of the illumination light from each lamp, different from that of the natural light.

Referring to FIG. 9, a color separation circuit 44' collectively represents the blocks designated reference numerals 44-49 shown in FIG. 3, and a post-process circuit 80 collectively represents the digital control and processing unit 47 and the digital encoder circuit 50 shown in FIG. 3. The crystal oscillator circuit 59 shown in FIG. 2 is represented by OSC 59. The remaining construction, operation and advantages of the second embodiment is identical to those of the first embodiment.

In this embodiment, the means for generating the ID information unique to the light source device 3A or 3B is arranged to set the white balance in accordance with the light source device 3A or 3B connected to the endoscope 2I in use. As represented by two-dot chain lines in FIG. 9, the endoscope 2I may be provided with a selection switch 81 to be switched in response to the light source device 3A or 3B, and a selection signal from the selection switch 81 may be used as a command signal (or ID information) to be fed to the DSP controlling computer 36 to set the white balance in response to the light source device 3A or 3B.

Besides the advantages of the first embodiment, in accordance with the present embodiment, an endoscopic examination is carried out in white balance states suitable to the light sources 3A and 3B which are different in color temperature (wavelength distribution).

The endoscope apparatus of the second embodiment presents images that faithfully reflect the color of a lesion in the body cavity of a subject or an internal structure of a piping when actually observed therethrough. Thus, for instance, the lesion in the body cavity of the subject is easily and properly diagnosed.

The gain setting circuit 71, the selector 72, and the A/D converters 73 and 74 are arranged corresponding to the light sources 3A and 3B in this embodiment. Alternatively, however, instead of these units, a programming tool may be connected to the serial terminal 18 to rewrite an operation program in the DSP controlling computer 36 to perform a similar job.

The white balance is set in accordance with the wavelength distributions of the light emitting lamps of the light sources 3A and 3B in this embodiment. The white balance is set in consideration of variations in the color separation filter of the CCD 26 and transmission characteristics dependent on the wavelength of the light guide 15.

Referring to FIG. 8, for instance, the R gain and B gain determined by the gain setting potentiometers 75r and 76r are set to be in the white balance state (with a white object picked up as a reference) when the light source device 3A or 3B is connected to the endoscope 2I. In this arrangement, the white balance is set in consideration of the characteristics of the light guide 15 and the CCD 26 in the endoscope 2I.

In accordance with the present embodiment, the CCU 29 is set to be compatible with the CCD 26 in the endoscope 2I as in the first embodiment. When the light guide 15 in the endoscope 2I has different characteristics or when the light source device connected to the endoscope 2I is changed, a proper white balance state is set.

Also as in the first embodiment, the CCU 29 includes the common DSP board 30 and the function adjustment/expansion circuit board 31, having a different setting so that the CCU 29 is compatible with the endoscope 2I even with the insertion length thereof different at a low cost involved. Furthermore, a proper white balance state is set regardless of variations, if any, in the color separation filter and the light guide 15.

Third Embodiment

Figure 10:
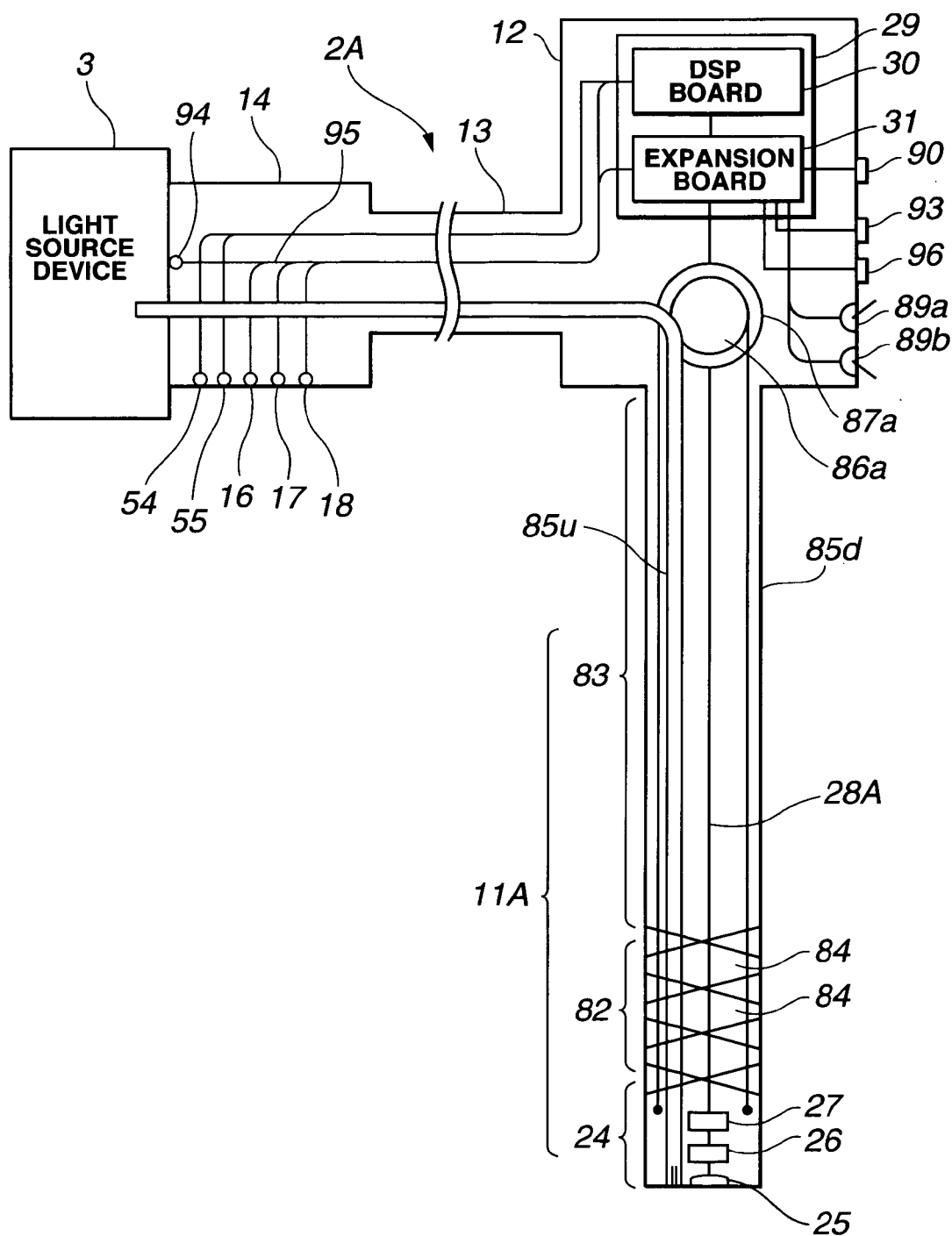
Figure 11:
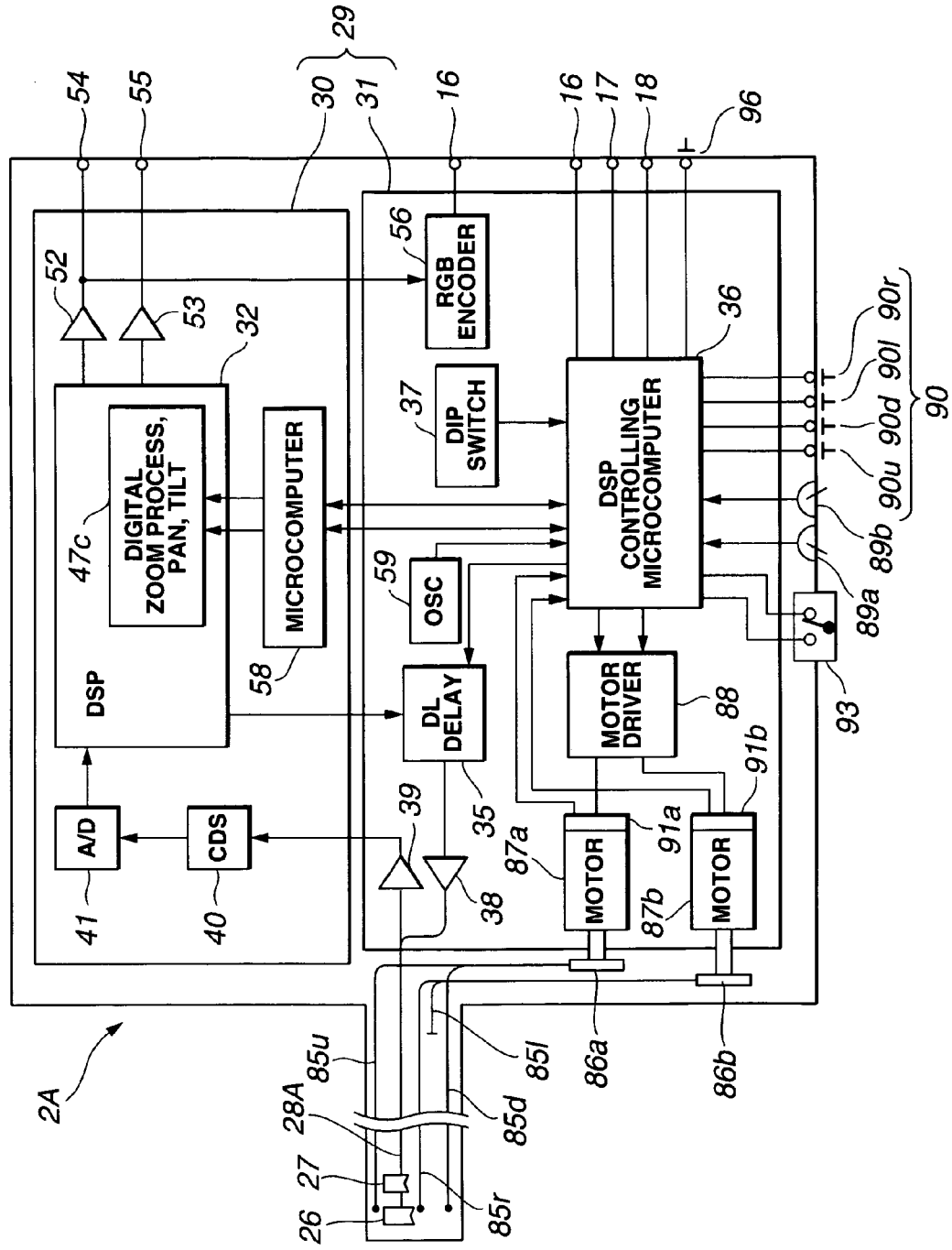

A third embodiment of the present invention is discussed referring to FIG. 10 and FIG. 11. FIG. 10 shows the construction of an endoscope apparatus of the third embodiment of the present invention with an endoscope 2A incorporated. FIG. 11 is a block diagram showing the construction of an electrical system of the endoscope apparatus.

In this embodiment, a motorized flexing mechanism is arranged in the endoscope 2I in the first embodiment.

An insert section 11A in the endoscope 2A shown in FIG. 10 includes an end portion 24, a bending portion 82 that is freely bent, and a flexible portion 83 having flexibility. The bending portion 82 is constructed of a plurality of barrel segments in a manner such that adjacent barrel segments 84 are bendably connected to each other in a cascade using link means such as rivets. The ends of a pair of angle wires 85u and 85*d* for bending the bending portion 82 are connected to the distal barrel segment at positions corresponding to the upward positions of the angle wires. The proximal ends of the angle wires 85*u* and 85*d* are entrained about a pulley 86*a* arranged in the control section 12. The pulley 86*a* is connected to an upward and downward bending motor 87*a*.

Left and right angle wires 85*l* and 85*r* (see FIG. 11) arranged on the left and the right, arranged 90 degrees away from the angle wires 85*u* and 85*d* within the insert section 11A are entrained about a pulley 86*b* within the control section 12 and the pulley 86*b* is connected a left and right bending motor 87*b*.

Referring to FIG. 11, the motors 87*a* and 87*b* are driven by a motor driver 88, which is in turn controlled by the DSP controlling computer 36.

The DSP controlling computer 36 is connected to an upward and downward bend direction control knob 89*a* and a left and right bend direction control knob 89*b*. By tilting the bend direction control knobs 89*a* or 89*b*, a command signal responsive to the command direction is input to the DSP controlling computer 36. The DSP controlling computer 36 outputs, to the motor driver 88, a control signal responsive to the commanded direction to cause the motor 87*a* or 87*b* to rotate. One of the angle wires 85*u*, 85*d*, 85*l*, and 85*r* is thus pulled, and the bending portion 82 is bent toward the angle wire 85*k* (k=u, d, l, and r).

With this arrangement, the bending portion 82 can be bent toward a desired direction with only a light force because of motorized driving, compared with a manual bending operation in which the angle wire 85*k* is pulled by hand.

The bend direction control knobs 89*a* and 89*b* are respectively tilted upward or downward, and leftward or rightward. These knobs may be replaced with a single joystick which is tilted in any direction upward or downward and leftward or rightward.

The rotary shafts of the motors 87*a* and 87*b* are respectively provided with encoders 91*a* and 91*b* to detect the amount of rotation of the motors 87*a* and 87*b*. The detected amount of rotation is input to the DSP controlling computer 36. Based on the detected amount of rotation, the DSP controlling computer 36 determines whether a commanded bend is achieved.

When the encoders 91*a* and 91*b* detect a maximum bend in each bend direction, the DSP controlling computer 36 stops the rotation of the motor 87*a* or 87*b*.

In this embodiment, a PAN function (scanning upward and downward) and a TILT function (scanning laterally) of a digital ZOOM processor 47*c* arranged in the DSP 32 for enlarging the image through signal processing are controlled in this way.

To this end, a control switch unit 90 is arranged. The DSP controlling computer 36 receives command signals from switches 90*u*, 90*d*, 90*l*, and 90*r* arranged in corresponding positions thereof in the control switch unit 90 when these switches are operated. An observed image is moved in a commanded direction and a function similar to the bending operation is thus performed.

Furthermore in this embodiment, a selection switch 93 is provided to switch between the angling operation by the bending operation knobs 89*a* and 89*b*, and the PAN and TILT operation.

For instance, when a maximum bend is achieved in the angling operation by the bending operation knobs 89*a* and 89*b*, followed by the angling operation function by the selection switch 93, and then the bending operation knobs 89*a* and 89*b* are operated in excess of the maximum bend angle, the PAN and TILT operations are controlled in the zoom operation so that the image is observed in excess of the maximum bending angle.

In this embodiment, the bending operation knobs 89*a* and 89*b*, and the control switch unit 90 are arranged on the control section 12 as shown in FIG. 10.

Furthermore in this embodiment, an unshown neutral switch is arranged to revert to a neutral position when the PAN and TILT operations are carried out in the zoom process.

Referring to FIG. 10, power is supplied from a power supply terminal 94 of the light source device 3 to the DSP board 30 and the function adjustment/expansion circuit board 31 (simply referred to as expansion board in FIG. 10) in the CCU 29 through a power supply line 95.

A main power switch 96 is arranged on the control section 12. FIG. 10 and FIG. 11 show the construction of the endoscope 2A, and the other endoscopes 2B and 2C also have the same construction. The remaining construction of this embodiment remains unchanged from that of the first embodiment.

In this embodiment, by operating the bend direction control knobs 89*a* and 89*b*, the bending portion 82 is bent toward a desired direction.

The operation of the control switch unit 90 permits observation in a direction beyond the maximum bend angle by the bend direction control knobs 89*a* and 89*b*. Ease of use is assured by the operation of the selection switch 93 so that observation is permitted in a direction beyond the maximum bend angle by the operation of the bend direction control knobs 89*a* and 89*b* only.

In this case, if the selection switch 93 is set to the PAN and TILT operation side, the bend direction control knobs 89*a* and 89*b* alone perform the PAN and TILT function.

The bending of the bending portion 82 is performed as follows.

When one of the bend direction control knobs 89*a* and 89*b* is moved, the DSP controlling computer 36 causes the motor 87*a* or 87*b* to rotate, thereby commanding the angling operation to operate. When the motor 87*a* or 87*b* rotates until the limit of angling operation, the motor 87*a* or 87*b* stops in response to the output of the encoder 91*a* or 91*b*.

Subsequent to the stop of the rotation of the motor 87*a* or 87*b*, the DSP controlling computer 36 sends the PAN and TILT of the digital ZOOM processor 47*c* of the DSP 32 to perform the PAN and TILT operation matching the bending command from the bend direction control knob 89*a* or 89*b*.

If the motorized bending operation and the PAN and TILT operations are interlocked, the operation of the bend direction control knobs 89*a* and 89*b* only permits observation in a direction in excess of the maximum bend angle, assuring the ease of use.

In a system power OFF operation, the DSP controlling computer 36 puts the motorized angle (of the bending portion 82) to a straight line state with the CCU 29 continuously outputting the video output, and then cuts off unshown DC output (power). In this automatic operation, the insert section 11I is pulled out of the subject being examined without exerting undue force to the angling mechanism.

This is the advantage that is achieved by the power source, the CCU 29, and the DSP controlling computer 36 for controlling the motorized angle under coordinated control.

The angle of the insert section 11I is controlled by an external personal computer 6 through communications. A sophisticated automatic angling operation is carried out, using video processing functions of the external personal computer 6.

Separate control SWs may be used to digitally control PAN and TILT operations.

Besides the advantages of the first embodiment, in accordance with the present embodiment, the bending portion 82 is easily bent toward a desired direction by operating the bend direction control knobs 89a and 89b arranged on the control section 12.

By operating the control switch unit 90, observation is permitted through the PAN and TILT of the digital ZOOM processor 47c.

In accordance with this embodiment, the zoom function (ZOOM, PAN, and TILT) by the DSP 32, and the motorized angle-related control are interlocked by the DSP controlling computer 36. Alternatively, with the selection switch 93 dispensed with, the motorized angle control by the bend direction control knobs 89a and 89b, and the PAN and TILT control in the digital zoom process by the control switch unit 90 may be independently performed.

Fourth Embodiment

Figure 12:
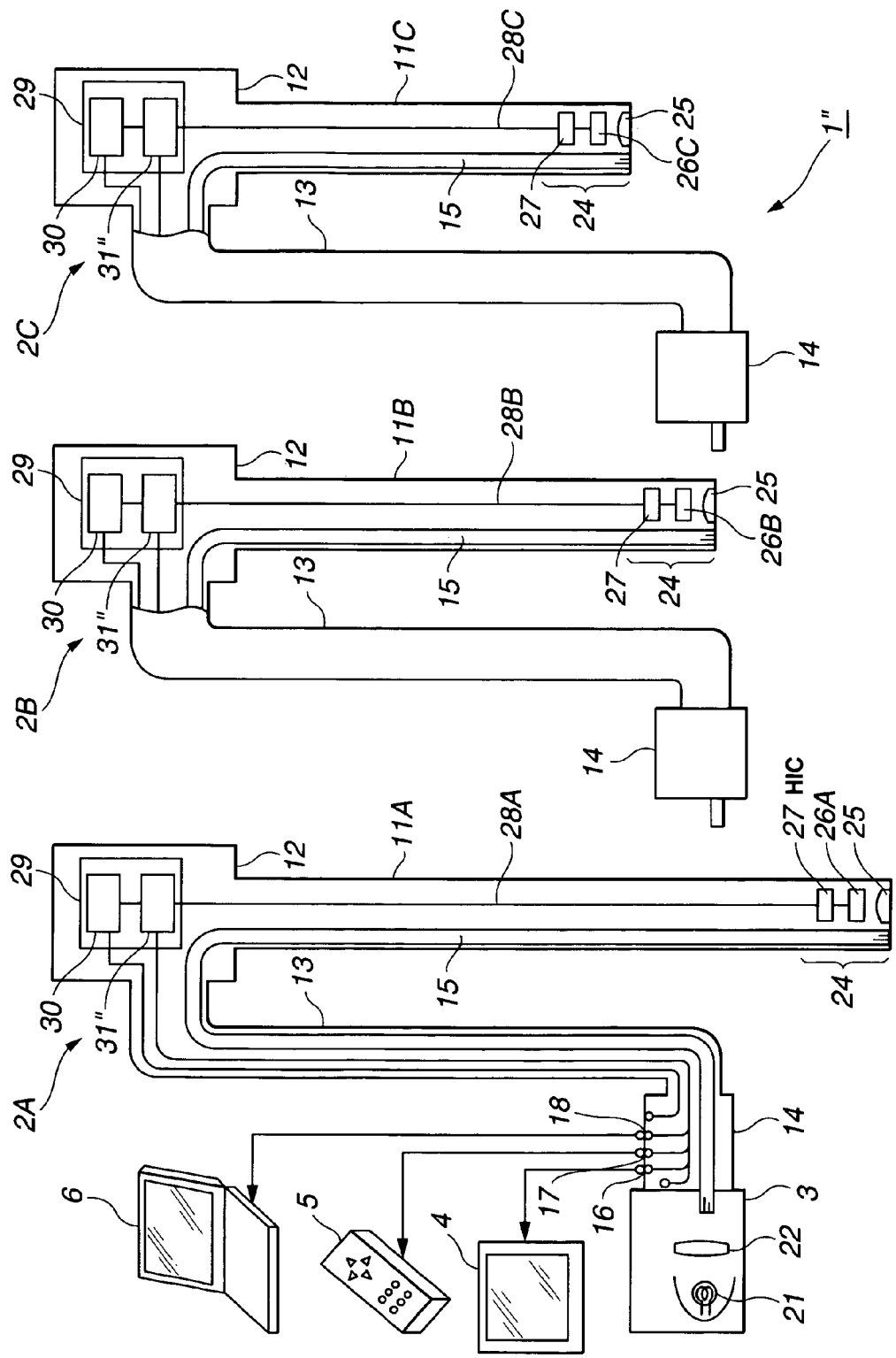
Figure 13:
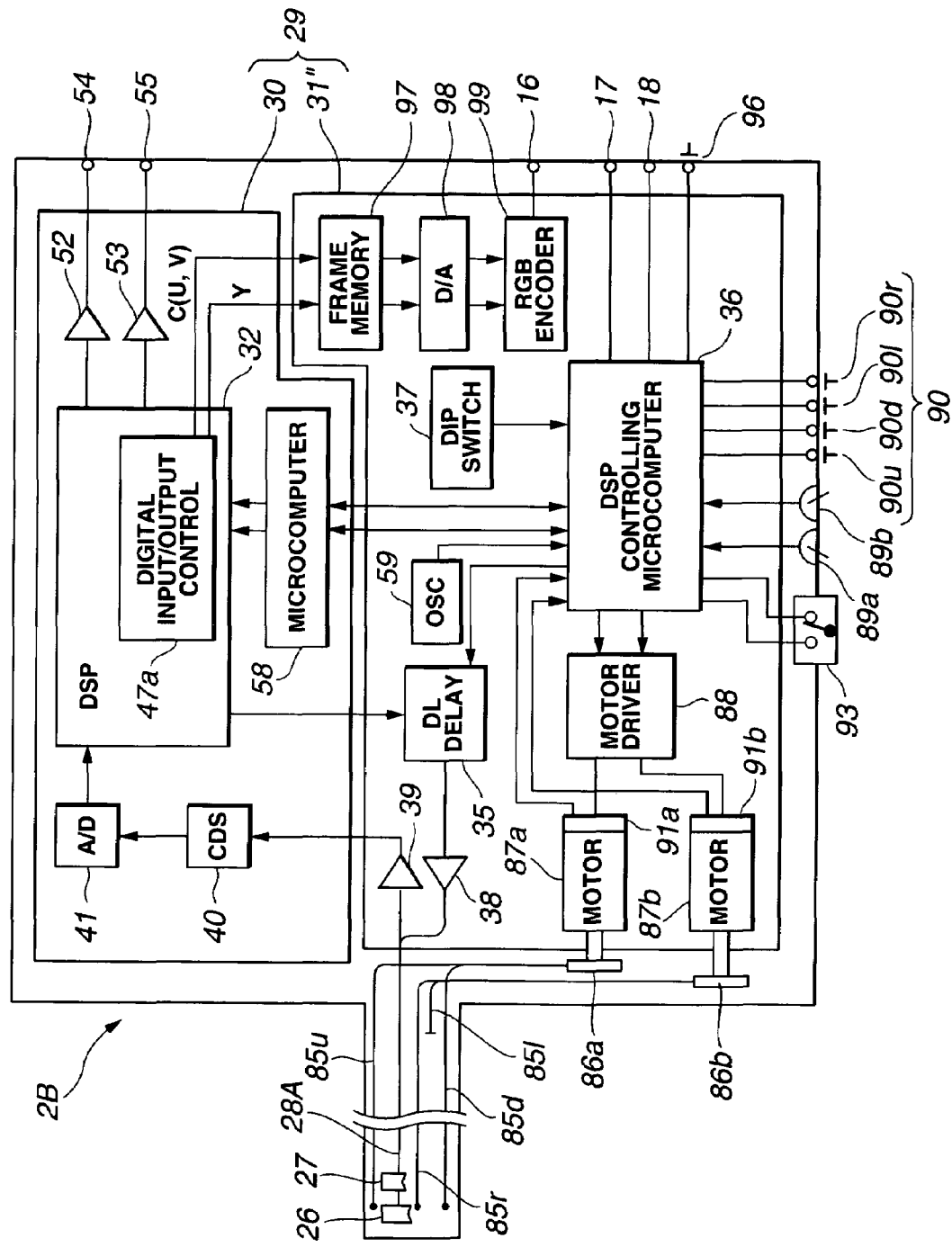
Figure 14:
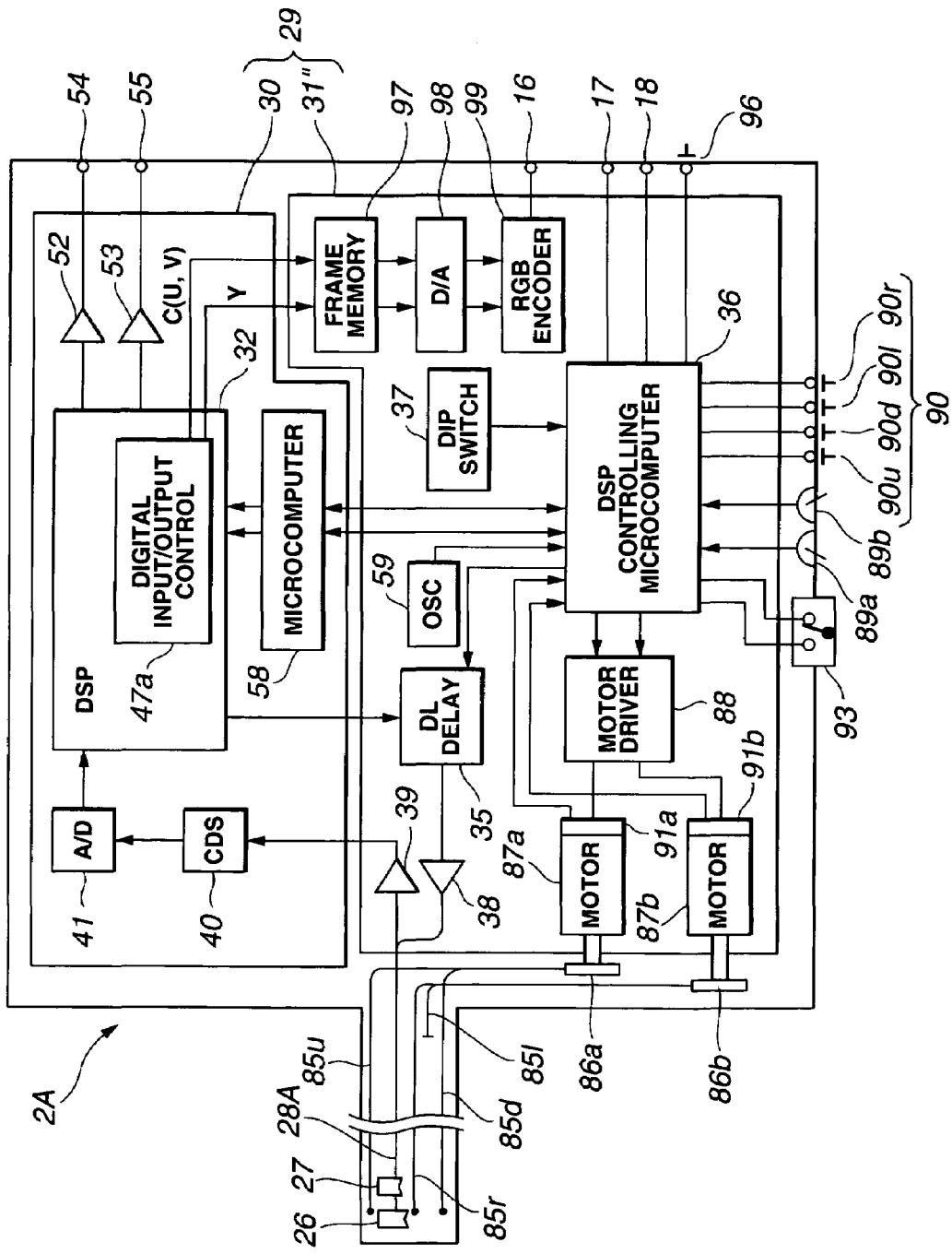
FIG. 14 is a block diagram showing the construction of an electrical system of an endoscope apparatus of a fifth embodiment of the present invention.

A fourth embodiment of the present invention is now discussed, referring to FIG. 12 through FIG. 14. This embodiment performs the signal processing compatible with a CCD having different number of pixels in the third embodiment.

FIG. 12 shows the construction of an endoscope system 1″ of the fourth embodiment of the present invention. In this embodiment, CCD 26A in an endoscope 2A, CCD 26B in an endoscope 2B, and CCD 26C in an endoscope 2C are different from each other in the number of pixels.

The number of pixels in both a horizontal direction and a vertical direction in the CCDs 26A, 26B, and 26C are related as follows: (the number of pixels of) CCD 26A>(the number of pixels of) CCD 26B>(the number of pixels of) CCD 26C. In other words, the CCD 26A has a maximum number of pixels.

The endoscope 2A with the CCD 26A having the maximum number of pixels has the same construction as the one shown in FIG. 11, and the discussion about it is omitted.

In the DSP board 30 combined with the CCD 26A having the maximum number of pixels, the crystal oscillator circuit 59 oscillates, giving a reference clock corresponding to the CCD 26A having the maximum number of pixels.

In the CCD 26B or CCD 26C having a smaller number of pixels than that of the CCD 26A, a standard video signal is generated even with a different number of pixels to output a signal to the liquid-crystal display monitor 4 by using the function adjustment/expansion circuit board 311, partly different from the function adjustment/expansion circuit board 31 in construction.

FIG. 13 shows the electrical system of the endoscope 2B (or 2C) that employs the CCD 26B (or 26C).

In the endoscope 2B shown in FIG. 1.3, a digital luminance signal Y and digital color signals C (color-difference signals U and V) output by a digital input and output controller 47a in the DSP 32 in the DSP board 30 of the endoscope 2A shown in FIG. 11 are temporarily stored in a frame memory 97 in the function adjustment/expansion circuit board 31″, then read from the frame memory 97 with a standard video period, and converted into an analog luminance signal Y and analog color signals C by a D/A converter 98. The analog luminance signal Y and analog color signals C are then converted by and RGB encoder 99 into an RGB signal, which is then output through a video output terminal 16.

The frame memory 97 has a memory capacity accommodating the CCD 26A having the maximum number of pixels (although the CCD 26B is also acceptable, the CCD 26A is used here so that the arrangement of this embodiment may be also used in the next embodiment).

The digital input and output controller 47a operates to output the digital luminance signal Y and digital color signals C corresponding to the number of pixels of the CCD 26A. When the CCD 26B (or CCD 26C) having the smaller number of pixels is used, the digital input and output controller 47a outputs a signal (a dummy signal) having no signal portion that is read from a portion beyond the pixels of the CCD 26B. The frame memory 97 stores the dummy signal for the portion beyond the number of pixels of the CCD 26B along with the signals for the pixels of the CCD 26B.

In other words, the frame memory 97 stores the dummy pixels in some of memory cells in the horizontal and vertical directions when the CCD 26B (or 26C) is used. When the signals are read therefrom, only the signals for the pixels are read under the control of the DSP controlling computer 36. The read digital luminance signal Y and color signals C are then converted by the D/A converter 98 into the analog luminance signal Y and analog color signals C, which are then converted into an RGB signal by the RGB encoder 99. The RGB signal is output through the video output terminal 16.

The display area thereof changes, depending on the number of pixels of the CCD 26I, in the liquid-crystal display monitor 4.

In the CCD 26B and CCD 26C having the smaller numbers of pixels, the area for the video display might become smaller. However, the digital ZOOM processor 47c in the DSP 32 varies the zoom magnification thereof to provide enlarged output to a TELE side. The size of the display area is substantially constant regardless of the number of pixels for the CCD. In this way, a video is presented on a full display screen regardless of the number of the pixels of the CCD.

In the CCD of a typical interline transfer standard TV signal (NTSC or PAL, for example), the number of pixels in the horizontal direction varies according to the number of pixels of the CCD, and the horizontal resolution thereof varies. Specifically, the larger the number of the pixels, the higher the resolution of the monitor. In the vertical direction, however, the number of pixels remains constant regardless of the changing number of pixels, and the vertical resolution remains constant regardless of the changing number of pixels. This is because the TV standards specify the constant number of scanning lines in the vertical direction.

If the CCD 26B or CCD 26C, having the smaller number of pixels, is driven by the DSP board 30, a vertically extending image with the horizontal size thereof contracted might be presented. To correct this, the digital ZOOM processor 47c increases the zoom magnification thereof in the horizontal direction to output an enlarged image to the TELE side. The image contracted in the horizontal direction is then again enlarged in the horizontal direction back to its original size. A normal display image is thus presented on a full display screen.

In this example, by varying the zoom magnification in the horizontal direction, the normal display image is restored regardless of the number of pixels of the CCD. The zoom magnification in the vertical direction may be set to be different from the zoom magnification in the vertical direction. In this arrangement, a normal display image is presented on a fully display screen if a CCD having any number of pixels is employed.

The DSP controlling computer 36 may store the zoom magnification for full display presentation. In this arrangement, the zoom magnification is transferred to the DSP 32 each time power is on in the endoscope 2B, and a full display presentation is operative from power on of the endoscope apparatus.

Besides the advantages of the third embodiment, in accordance with this embodiment, the same DSP board 30 and the function adjustment/expansion circuit board with its construction slightly modified work with the CCD 26I having a different number of pixels.

Fifth Embodiment

A fifth embodiment of the present invention is now discussed, referring to FIG. 14. The fifth embodiment is constructed by adding a freeze function to the fourth embodiment.

In this embodiment, the endoscope 2A employs the function adjustment/expansion circuit board 31" as in the other endoscopes 2B and 2C in the fourth embodiment. Specifically, when the number of pixels is different, the common function adjustment/expansion circuit board 31" in the endoscope 2A (the other endoscopes 2B and 2C) shown in FIG. 14 is employed.

In this embodiment, a freeze switch 92 is arranged on the control section 12. A freeze command signal is fed to the DSP controlling computer 36 in response to the operation of the freeze switch 92. The DSP controlling computer 36 inhibits the writing onto the frame memory 97.

The signal, which was written onto the frame memory 97 immediately prior to the inhibition, is repeatedly output and a still image is thus presented on the liquid-crystal display monitor 4. When the freeze switch 92 is operated after the still image is presented, the write inhibition is released. A moving image signal is then output from the frame memory 97.

Besides the advantages of the fourth embodiment, in accordance with the present embodiment, the same DSP board 30 and the function adjustment/expansion circuit board with its construction slightly modified work with the CCD 26I having a different number of pixels, and a still image is presented.

The fourth embodiment may be provided with the function of presenting a still image when the endoscope 2B or 2C employing the frame memory 97 is used.

Although the common DSP board 30 is employed in the fourth and fifth embodiments even when the number of pixels is employed, the following arrangement may be contemplated. The crystal oscillator circuits 59 for feeding the reference clock is arranged for cases of the different number of pixels, and are switched to feed the reference clock to the DSP 32. A plurality of bandwidth limiting LPFs for the D/A converter circuit 51, which are optimized for characteristics for the plurality of pixel number settings, are arranged on the DSP board 30, and are switched for use. In this arrangement, the CCD having any number of pixels is driven at an optimum drive frequency, and the display area does not change, permitting a full display image to be presented.

Furthermore, to cope with the different numbers of pixels, a software modification may be introduced in the DSP controlling computer 36 in the function adjustment/expansion circuit board 31 and a constant modification may be introduced in the CCD drive circuit.

An automatic lighting adjustment mechanism may be introduced to automatically set the average luminance level of a picked signal to be a target luminance level in the lighting control of the illumination light of the light source.

Embodiments including a combination of part of the above embodiments fall within the scope of the present invention.

It is obvious that a variety of embodiments are constituted without departing from the spirit and scope of the present invention. The present invention is limited by the appended claims only, and is not limited by any specific embodiment.

What is claimed is:

1. An endoscope, comprising:
an elongated insert section;
a solid-state image pickup device for picking up an image, the solid-state image pickup device being provided to an end portion of the insert section;
a general-purpose video signal processing circuit including a drive signal generating section for generating a drive signal for driving the solid-state image pickup device, and a video signal processing section for producing a standard video signal in response to an output signal outputted from the solid-state image pickup device,
wherein the general-purpose video signal processing circuit is mounted on a first common board along with a first microcomputer that performs operation setting of the general-purpose video signal processing circuit;
an adjusting circuit including a timing adjusting section for performing timing adjustment of the drive signal by receiving and thereafter delaying the drive signal generated by the drive signal generating section in accordance with a delay time and transmitting the delayed drive signal to the solid-state image pickup device such that the output signal to be inputted to the general-purpose video signal processing circuit has a correct timing, and a signal processing adjusting section for adjusting signal processing with respect to the video signal processing section,
wherein the adjusting circuit is mounted on a second common board along with a second microcomputer for controlling the adjusting circuit, and
wherein the first microcomputer is connected to the second microcomputer through an interface; and
a video signal output connector for outputting the standard video signal outputted from the general-purpose video signal processing circuit to an external display unit.

2. The endoscope according to claim 1, wherein the general-purpose video signal processing circuit and the adjusting circuit are disposed in an operational section arranged at a proximal end of the insert section.

3. The endoscope according to claim 1, wherein the adjusting circuit is mounted on a second common board along with a second microcomputer for controlling the adjusting circuit.

4. The endoscope according to claim 1, wherein the timing adjusting section comprises a delay amount adjusting circuit which receives the drive signal generated by the drive signal generating section and a signal corresponding to an amount of a delay time and thereafter delays the received drive signal and transmits the delayed drive signal to the solid-state image pickup device.

5. The endoscope according to claim 4, wherein the amount of delay time that the drive signal is delayed by the delay amount adjusting circuit corrects a time delay for the drive signal outputted by the drive signal generating section to be applied to the solid-state image pickup device and a time delay for the output signal outputted from the solid-state image pickup device to be inputted to the video signal processing section, to input the output signal to the video signal processing section at a predetermined timing.

6. The endoscope according to claim 1, wherein the general-purpose video signal processing circuit comprises a digital signal processor.

7. The endoscope according to claim 1, wherein the end portion includes a wave shaping circuit for performing wave shaping of the drive signal timing-adjusted by the timing section and applying the wave-shaped drive signal to the solid-state image pickup device.

8. The endoscope according to claim 1, further comprising a light guide for transmitting illumination light, an end portion of the light guide being detachably connected to an external light source device.

9. The endoscope according to claim 1, wherein the signal processing adjusting section comprises a pixel-number signal adjusting section for adjusting signal processing by the video signal processing section compatibly with different numbers of pixels of the solid-state image pickup device.

10. The endoscope according to claim 1, further comprising an electrical bending driving section for controlling bending of a bending portion provided to the insert section.

11. The endoscope according to claim 1, further comprising an external remote control circuit detachably connected to the endoscope.

12. The endoscope according to claim 1, wherein the video signal output connector outputs a plurality of standard video signals of different types.

13. The endoscope according to claim 1, further comprising a connecting terminal for a remote control provided outside the endoscope for remote-controlling the general purpose video signal processing circuit.

14. An endoscope comprising:
an elongated insert section;
a solid state image pick up device for picking up an image, and the solid-state image pickup device being provided to an end portion of the insert section;
a general-purpose video processing circuit including a drive signal generating section for generating a drive signal for driving the solid-state image pickup device, and a video signal processing section for producing a standard video signal in response to an output signal outputted from the solid-state image pickup device;
an adjusting circuit including a timing adjusting section for performing timing adjustment of the drive signal generated by the drive signal generating section such that the output signal to be inputted to the general-purpose video processing circuit has a correct timing, and a signal processing adjusting section for adjusting signal processing with respect to the video signal processing section; and
a video signal output connector for outputting the standard video signal outputted from the general-purpose video signal processing circuit to an external display unit; wherein the general-purpose video signal processing circuit is mounted on a first common board along with a first microcomputer that performs operation setting of the general-purpose video signal processing circuit, the adjusting circuit is mounted on a second common board alone with a second microcomputer for controlling the adjusting circuit, and the first microcomputer is connected to the second microcomputer through an interface.

* * * * *